United States Patent [19]

Michaels

[11] 4,340,054
[45] Jul. 20, 1982

[54] DISPENSER FOR DELIVERING FLUIDS AND SOLIDS

[75] Inventor: Alan S. Michaels, San Francisco, Calif.

[73] Assignee: ALZA Corporation, Palo Alto, Calif.

[21] Appl. No.: 220,789

[22] Filed: Dec. 29, 1980

[51] Int. Cl.³ .............................................. A61M 7/00
[52] U.S. Cl. ..................................... 128/260; 222/95;
  222/105; 222/214; 222/386.5
[58] Field of Search ................................ 128/127–131,
  128/260–261; 222/95, 105, 214, 386.5

[56] References Cited

U.S. PATENT DOCUMENTS

| | | | |
|---|---|---|---|
| 3,760,805 | 9/1973 | Higuchi | 128/260 |
| 3,828,777 | 8/1974 | Ness | 128/260 |
| 3,995,631 | 12/1976 | Higuchi et al. | 128/260 |
| 4,111,201 | 9/1978 | Theeuwes | 128/260 |
| 4,111,202 | 9/1978 | Theeuwes | 128/260 |
| 4,111,203 | 9/1978 | Theeuwes | 128/260 |
| 4,309,996 | 1/1982 | Theeuwes | 128/260 |

*Primary Examiner*—C. Fred Rosenbaum
*Attorney, Agent, or Firm*—Paul L. Sabatine; Edward L. Mandell

[57] ABSTRACT

An osmotically driven fluid dispenser is disclosed comprising a flexible container having a port for filling and emptying same, a layer of an osmotically effective solute on the container, and a shape retaining microporous housing having a fluid rate controlling material in its micropores. The dispenser can be used for delivering fluids and solid agents, and as a displacement pump.

15 Claims, 2 Drawing Figures

DISPENSER FOR DELIVERING FLUIDS AND SOLIDS

FIELD OF THE INVENTION

This invention pertains to an improvement and modification of an osmotically driven agent dispenser.

THE PRIOR ART

The prior art has provided commercially important dispensers that are useful for delivering beneficial agents to environments of use. For example, U.S. Pat. No. 3,760,984 issued to patentee Theeuwes discloses a dispenser comprising an inner chamber formed of a heat shrinkable polymer carrying on its outer surface an osmotic solute, and a distant layer of a semipermeable polymer permeable to the passage of a fluid and substantially impermeable to the passage of solute.

The dispenser has a means for filling the chamber. In U.S. Pat. No. 3,865,108, patentee Hartop describes a dispenser that operates by absorbing water. The components of this dispenser are arranged concentrically and they consist of an inner collapsible tube that contains a medicine, a water swellable base that surrounds all but one end of the tube, and an optional water permeable outer skin around the base for keeping it intact. In U.S. Pat. No. 3,987,790 issued to patentee Eckenhoff et al, there is disclosed an improvement in osmotic dispenser consisting of a conduit for filling the dispenser. In U.S. Pat. No. 3,971,376 issued to Patentee Wichterle a dispenser is claimed consisting of a capsule having unitary walls formed of a substantially non-collapsible material that is exposed to the environment of use. A textile fabric is imbedded in the material for imparting strength and minimizing problems due to the poor mechanical properties of the material that occur during fluid uptake. In U.S. Pat. No. 3,995,631 patentee Higuchi et al, discloses a bag bearing on its outer surface a layer of an inorganic solute, and a distant wall formed of a material having part controlled permeability to fluid.

The dispensers described in the above patents are useful for delivering numerous agents to many environments of use, and they represent an advancement in the delivery art. Generally, the dispensers of the prior art use a semipermeable wall for admitting fluid into the dispenser for forming a solution of solute that powers the dispenser; and, for these dispensers the rate of fluid admitted into the dispenser is controlled by the permeability of the wall and the osmotic pressure gradient across the wall. Thus, the application and kinds of agents that can be delivered by these dispensers is governed by their physical and chemical properties. The present invention contributes to the delivery art by providing a dispenser comprising a wall that can house a multiplicity of different materials for admitting fluid to the dispenser, thereby increasing the application and kinds of agents that can be dispensed from the dispenser.

OBJECTS OF THE INVENTION

It is an immediate object of this invention to provide a novel and useful dispenser for dispensing a beneficial agent for producing a useful effect, and which dispenser additionally contributes improvements and modifications to the prior art.

It is a further object of this invention to provide a dispenser for delivering a beneficial agent to produce a beneficial effect, which dispenser overcomes the limitations known to the prior art.

Yet another object of the invention is to provide a dispenser that is self-powered, easy to manufacture, and can be used for dispensing beneficial agents to animals including humans, and into other biological and non-biological environments of use.

Still another object of the invention is to provide a dispenser having a wall that can house different material in the wall for admitting fluid into the dispenser, thereby providing a means for increasing the range of agents that can be delivered by selecting an appropriate material for a given agent.

Yet another object of the invention is to provide a dispenser comprising a microporous wall whose pores house a material for selectively admitting a fluid into a dispenser that uses an osmotic solute as its power generating force.

Yet another object of the invention is to provide a dispenser comprising a microporous wall having its pores charged with a material for admitting fluid into the dispenser, and which microporous wall can be used with an osmotically effective solute for powering a fluid tight dispenser that can deliver fluids and solids.

Another object of the invention is to provide a dispenser that is empty until filled with agent, and when filled can administer a complete pharmaceutical dosage regimen for a period of time the use of which requires intervention only for initiation and termination of the regimen.

It is a further object of the invention to provide a dispenser that can be manufactured as a drug delivery device, and which device can operate to yield results substantially equivalent to those obtained with a sustained release method of drug administration.

Other objects, features and advantages of the invention will be more apparent to those skilled in the delivery art, from the detailed description of the specification, taken in conjunction with the drawings and the accompanying claims.

SUMMARY OF THE INVENTION

This invention concerns a dispenser for delivering an agent to an environment of use. The dispenser comprises an intermediate layer of an osmotically effective solute that at least partly covers an inner flexible container having an exit port. The container is made of an elastomeric material for storing an agent. The intermediate layer is surrounded by a wall of a microporous material having its pores charged with a material that admits fluid into the dispenser. In operation, the dispenser delivers agent by the wall admitting fluid into the dispenser to dissolve and form a solution of solute, which solution exerts a mechanical compressing or deflating force on the flexible container, and thereby urges the agent through the port from the dispenser.

BRIEF DESCRIPTION OF THE DRAWINGS

In the drawings, which are not drawn to scale, but are set forth to illustrate various embodiments of the invention, the figures are as follows.

In the drawings and the specification, like parts in related Figures are identified by like numbers. The terms appearing earlier in the specification, and in the drawings, as well as embodiments thereof, are further described elsewhere in the disclosure.

DETAILED DESCRIPTION OF THE DRAWINGS

Figure 1:
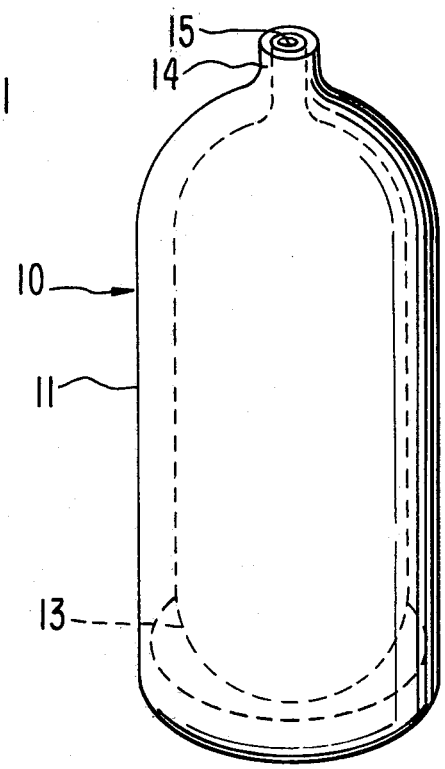
FIG. 1 is a side, elevational view illustrating a dispenser made according to the invention; and, FIG. 2, taken in conjunction with FIG. 1, illustrates the dispenser in opened section for illustrating the structure of the dispenser.
Figure 2:
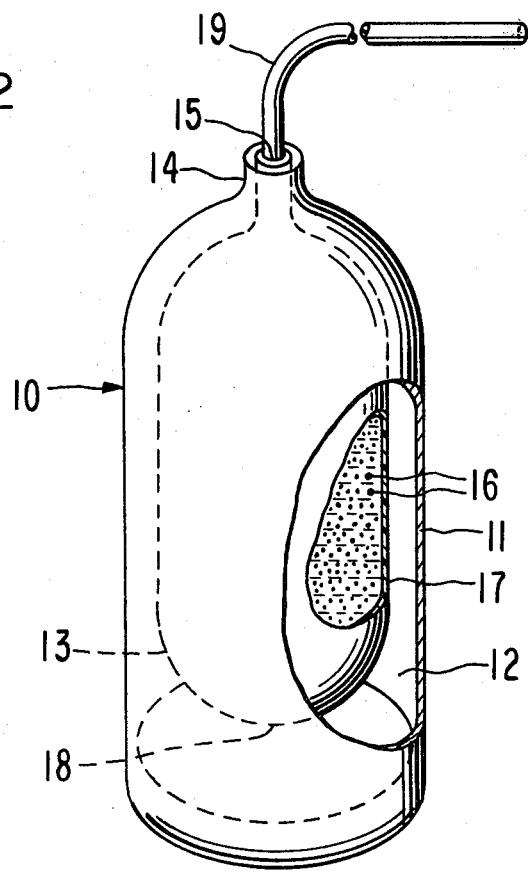

Turning now to FIG. 1 and FIG. 2 taken together, which are an example of a new and useful dispenser for delivering an agent including drug, and which example is not to be construed as limiting, one dispenser is illustrated in FIGS. 1 and 2 by the numeral 10. In the Figures, dispenser 10 comprises a wall or exterior housing 11 that is shaped, sized and adapted for placing dispenser 10 in a preselected environment of use. Wall 11 surrounds and forms an internal space 12, seen in FIG. 2, that has a section of wall 11 removed for depicting the structure of dispenser 10. Wall 11 is made from a microporous polymeric material whose pores house a fluid rate controlling material that governs the entry of an exterior fluid into dispenser 10. Wall 11, in addition to governing the volume of fluid admitted into dispenser 10, also imparts physical integrity and structure to dispenser 10 throughout the dispensing period.

Wall 11 is made from a microporous polymeric material whose pores house a material that regulates the volume of fluid that enters the dispenser. Generally, the microporous polymers have from 5 to 50% of pores interconnected through tortuous paths which extend from one surface of wall 11 to the other surface of wall 11. Generally, the microporous polymers having a pore size of from 10 angstroms to 10 microns can be used for manufacturing the dispenser. The microporous polymers can embrace structure characteristics of microporous polyolefins, polyamides, polycarbonates, polyesters, polystyrenes, polysulphones, polyimides, polyvinyls, polyarylenes, polyaldehydes, polyarylates, polyhaloolefins, polyacetats, polyacrylates, polyurethanes, the homopolymers and the copolymers thereof, and the like. Procedures for preparing microporous polymers are described in *Synthetic Polymer Membranes* by R. E. Kesting, Chapters 4 and 5, 1971, published by McGraw Hill, Inc.; in *Chemical Reviews*, Vol. 18, pages 373 to 455, 1934, in *Polymer Eng. and Sci.*, Vol. 11, pages 811 to 829, 1971; and in U.S. Pat. Nos. 3,565,259; 3,615,024; 3,751,536; 3,801,692; 3,852,244; 3,849,528; and 4,160,452.

The pores of the polymer can be filled with a hydrophilic, or a hydrophobic material that exhibits selective permeability to the passage of water. Representative materials include glycerin, ethylene glycol, propylene glycol, methyl cellulose mixed with cellulose acetate, mixtures of propylene glycol monostearate and oils, gum tragacanth, polyoxyethylene stearate, alkylene diols wherein the alkylene has 2 to 10 carbons such as poly(1,5)-pentanediol, polyesters of alkylene glycols and a monobasic or dibasic acid such as ethylene glycol diacetate, and the like. The material can be added to the pores by immersion of a microporous polymeric film in a bath containing the material to let it fill the micropores. The material can be added to the polymer during casting of the polymer. For example, pulverized solid, cross-linked polymethylmethacrylate, an isoluble swellable polymer that allows for the presence of water, is added to a polymer dissolved in a solvent, such as ethylene vinyl-acetate copolymer in methylene chloride, with the copolymer cast and the solvent evaporated to leave a film that functions with microporous characteristics. The micropores of a polymeric film, for example a film of polyhexamethylene adipamide, can be charged by spreading and working into the pores hydroxyethyl methacrylate-ethylene glycol dimethacrylate dissolved in diacetine, followed by evaporation and wiping the film clean. The micropores also can be filled with a hydrogel cross-linked in the pores. For example, the hydrogel can consist of a sparingly cross-linked copolymer of a monoester of an olefinic acid and a polyfunctional alcohol having an esterifiable hydroxyl group and at least one additional hydrophilic functional group, with a diester of an olefinic acid and an alcohol having at least two esterifiable hydroxyl groups. Exemplary olefinic acids include acrylic and methacrylic acids, and exemplary alcohols include polyalkylene glycol, trialkanolamine, polyvinyl alcohol, and the like. The micropores of a polymer for example polyvinyl chloride can be filled with a hydrogel by copolymerizing a glycol and a mono or di(meth) acrylate in a solvent in the pores, followed by irradiating with x or gamma rays. The micropores of a polymer also can be filled with the hydrophilic polymers disclosed later in the specification. Generally, the microporous wall will have a thickness, depending on the device and its use, of from about 0.01 mm to 7 mm, or more.

Dispenser 10 houses an inner flexible container 13 identified by continuous dashed lines in FIGS. 1 and 2, and seen in opened section in FIG. 2. Container 13 has a lead end 14 that forms and defines a port 15 for filling container 13, or for delivering an agent 16, identified by dots and dashes, from container 13 to the exterior of dispenser 10. Container 13 houses beneficial agent 16 substantially free from any adverse effects on the agent. Container 13 also can house agent 16 over a prolonged period of time sheltered from any possible adverse action arising in the environment of use. Port 15 is preferrably formed during the manufacture of container 13, and it has internal dimensions selected for assisting in governing the rate of release of agent 16 from dispenser 10. Port 15 also is adapted for receiving a tube that fits snugly into port 15 for filling or dispensing agent 16 from dispenser 10. Container 13 has a trailing end 18 and it carries on its exterior surface a layer in whole or in at least a part of an osmotically effective solute. Container 13 has a wall 17 made of an elastomeric material, that can change its dimensions over time, and more particularly, can collapse in response to pressure applied against the exterior surface of container 13.

Representative materials suitable for manufacturing container 13 are materials that can be designed into a shaped container, structured as an elastomeric tube or bag, which collapses in response to externally applied pressure, thereby dispensing agent 16. Typical elastomeric polymers include natural rubber, often identified by the synonyms poly(2-methyl-1,-3-butadiene) and cis-1,4-polyisoprene, gutta percha or transpolyisoprene, cyclized rubber, silicone rubber, synthetic isoprene rubber, butadiene rubber, copolymeric styrene-butadiene rubbers, nitrile rubber, chloroprene rubber, ethylene-propylene rubbers, butyl rubbers, and the like. These elastomric materials are disclosed in *Handbook of Common Polymers*, by Scott and Roff, Sections 29 through 40, 1971, published by the Chemical Rubber Co., Cleveland, Ohio. Container 13, formed of the above representative materials, can have a wall of varying thickness, usually about 0.001 mm to 7 mm, or more depending on the container and the use of device 10. Container 13 is manufactured with a passageway for dispensing agent 16 and it can be made to form a passageway when dispenser 10 is in the environment of use. Passageway 15 will have a cross-section of 1 to 20 mils. When Passageway 15 is formed in the environment of use, it is closed with a water-soluble plug of an erodible material, such as noncross-linked poly(vinyl alcohol), gelatin or the like that erodes to form the passageway. The end of container 13 including passageway 15 can also receive tube or conduit 19, for transporting agent dispensed from the dispenser to a receiving site located away from the dispenser.

The osmotically effective solute carried on the exterior surface of wall 17 of container 13 and facing the interior surface of wall 11 of dispenser 10 are selected from organic and inorganic compounds that are soluble in fluid that enters the dispenser, can dissolve and form a solution, and exhibit an osmotic pressure gradient across wall 11 against an external fluid. Suitable solutes include magnesium, sulfate, magnesium chloride, sodium chloride, lithium chloride, potassium sulfate, sodium carbonate, potassium carbonate, sodium sulfite, lithium sulfate, calcium bicarbonate, sodium sulfate, calcium sulfate, potassium acid phosphate, calcium lactate, magnesium succinate, tartaric acid, soluble carbohydrates such as raffinose, glucose, and the like. The solute can be mixed with a water soluble binder for applying to the wall of the container. Typical binders include water soluble gelatin and soluble starch derivatives.

Exemplary of useful agents that can be housed in the container and delivered from the dispenser include fluids, semisolids and solids. The term fluid includes water, saline, buffers and the like. The semisolids and solids agent includes algicides, anti-oxidants, air purifiers, biocides, bactericides, catalysts, chemical reactants, cosmetics, disinfectants, drugs, fungicides, flavoring agents, foods, food supplements, fertility inhibitors, fermentation agents, fertility promoters, germicides, insecticide, microorganism alternators, nutrients, pesticides, plant growth promoters, plant growth inhibitors, preservating agents, slimicides, surfactants, sterilization agents, sex sterilants, vitamins, and other like agents that benefit animals and man.

Exemplary drugs that can be administered according to the spirit of the invention include locally and systemically acting drugs. These drugs include a member selected from the group consisting of physiologically and pharmacolgically acting drugs such as gastrointestinal administrable drugs, central nervous system acting drugs, hypnotic, sedative, psychic energizer, tranquilizer, anticonvulsant, anti-parkinson, muscle relaxant, analgesic, antipyretic, anti-inflammatory, aensthetic, antispasmodic, antimicrobial, antiviral, antiucler, hormonal, sympathomimetic, diuretic, hypoglycermic, vitamins, contraceptive, and opthalmic drugs. These beneficial drugs and their dose amounts for humans are known to the art in *Drills' Pharmacology In Medicine*, edited by DiPalma, Joseph R., 1965, published by McGraw-Hill Book Company, New York, in *Pharmacological Basis of Therapeutics*, by Goodman and Gilman, 4th Edition, 1970, published by MacMillian Co., London, and in U.S. Pat. No. 3,977,404, which patent is assigned to the ALZA Corporation of Palo Alto, Calf., the assignee of this application. The drug in the container can be mixed with a pharmaceutically acceptable liquid such as water, saline, cottonseed oil, sesame oil, ethylene oleate, isopropyl myristate, propylene glycol, and the like. The drug can be present in solution, in semi-solid or paste formulation, in a thixotropic state and the like, which form permits controlled dispensing of drug from the device. Pharmaceutically acceptable carriers and the like are known to the art in *Remington's Pharmaceutical Science*, 14th Edition, pages 1461 to 1762, 1970, published by the Mack Publishing Company, Easton, Pa.

While FIGS. 1 and 2 are illustrative of various systems that can be made according to the invention, it is to be understood these systems are not to be construed as limiting, as they can take a wide variety of shapes, sizes and forms adapted for delivering an agent including drug to many and varied different environments of use. For example, system 10 can be manufactured for dispensing drug to animals, which term includes warm-blooded mammals, humans, household, farm, sport and zoo animals. The dispensers can also be used for dispensing drugs to avians, fishes and reptiles. Dispensing dispenser 10 can be sized, shaped and adapted for dispensing drug to body cavities and body openings, and for uses including oral administration, intramuscular implants, intrauterine, vaginal, cervical, rectal, nasal, ear, and dermal applications. Dispenser 10 also can be used as an artificial gland, and for arterial and venous administration of drug. The dispenser can be made for use in homes, hospitals, nursing homes, clinics, ships, laboratories, factories and the like.

An improved dispensing dispenser embracing the structural members acting together is manufactured as follows: first, a cylindrical shaped container 2.33 cm long, 3.81 inside diameter and 4.67 mm outside diameter, is injection molded at 180° C., at 77–84 kg/cm$^2$, from the elastomeric copolymer styrene-butadiene. Next, a mandrel is inserted into the container, and the container dipped into a suspension of potassium sulfate in dioxane-gelatin solution, 50 wt%, to a depth of 1.8 cm at least 4 times for 1 minute per dip with an intervening 15 minute room air drying period. The dipping coated the container with an approximately 0.4 mm thick coating of the osmotically effective solute. Next, the coated container is placed inside a thin walled tube of microporous polypropylene having its pores charged with crosslinked hydrophilic polymer of hydroxyethyl methacrylate and ethylene dimethacrylate, and the tube tightly sealed at its trailing end and at its lead end around the port of the container.

Dispenser 10 operates in an aqueous environment, such as within a body cavity, by water from the environment being imbibed by the layer of solute through micropores at a rate determined by the osmotic activity of the solute, and the osmotic reflection coefficient, composition, thickness and area of wall 11. The imbibed water causes the volume of the space between the inner surface of wall 11 and the exterior of container 13 to increase. And since wall 11 is shape retaining, the imbibed water generates hydraulic pressure on the exterior of container 13 causing it to be squeezed inwardly. This squeezing force agent 16 through port 15 and out of dispenser 10. When tube 19 is attached to dispenser 10, the dispenser can deliver an agent to a distant receptor site, and alternatively, the dispenser housing a fluid may be used simply as a displacement pump. Representative of a drug formulation that can be housed in the container and dispensed to a biological environment over time is tetracycline hydrochloride in polyethylene glycol 200.

Modifications of the above described dispenser that are obvious to those skilled in the mechanical, chemical and other related arts are intended to be within the scope of the following claims.

I claim:

1. In an osmotically driven dispenser comprising an inner flexible container adapted to contain a useful agent, an intermediate layer of an osmotically effective solute at least partly covering the container, and an outer shape-retaining microporous membrane surrounding the layer of osmotically effective solute, said microporous membrane housing in its micropores a material permeable to the passage of fluid, and a port that extends from the interior of the container to the exterior of the dispenser though which agent may be charged into the container and dispensed from the container over time.

2. The osmotically driven dispenser according to claim 1, wherein the port is adapted for receiving a tube that fits snugly into the port.

3. The osmotically driven dispenser according to claim 1, wherein the container is formed of an elastomeric polymer movable from an expanded state to a collapsed state over time.

4. The osmotically driven dispenser according to claim 1, wherein the osmotically effective solute and the material permeable to the passage of fluid in the micropores act together for regulating the rate of fluid admitted into the dispenser.

5. The osmotically driven dispenser according to claim 1, wherein the material in the micropores is a hydrophilic, crosslinked polymer.

6. The osmotically driven dispenser according to claim 1, wherein the material in the micropores is a hydrophobic, crosslinked polymer.

7. The osmotically driven dispenser according to claim 1, wherein the agent housed in the container is a fluid.

8. The osmotically driven dispenser according to claim 1, wherein the container houses an agent that is a drug, which drug is present in solution, in semi-solid, or in a thixotropic formulation.

9. The osmotically driven dispenser according to claim 1, wherein the dispenser is sized, shaped, and adapted for use in rectal passageway.

10. The osmotically driven dispenser according to claim 1, wherein the dispenser is sized, shaped and adapted for use in the gastrointestinal track.

11. The osmotically driven dispenser according to claim 1, wherein the dispenser is sized, shaped and adapted for use in a vagina.

12. The osmotically driven dispenser according to claim 1, wherein the dispenser is sized, shaped and adapted for use as an implant.

13. The osmotically driven dispenser according to claim 1, wherein the container houses an agent that is a drug, said drug a member selected from the group consisting of locally and systemically acting drugs.

14. The osmotically driven dispenser according to claim 1, wherein the osmotically effective solute is mixed with a water soluble binder.

15. The osmotically driven dispenser according to claim 1, wherein the container is formed of a member selected from the group consisting of natural rubber, isoprene rubber, butadiene rubber, styrene-butadiene rubber, nitrile rubber, chloroprene rubber, ethylene-butylene rubber, and butyl rubber.

* * * * *